US00PP36760P3

(12) United States Plant Patent
Hopmans

(10) Patent No.: US PP36,760 P3
(45) Date of Patent: Jun. 24, 2025

(54) ***HEBE* PLANT NAMED 'HOP107'**

(50) Latin Name: ***Hebe speciosa Hebe* Comm. ex. Juss**
Varietal Denomination: HOP107

(71) Applicant: FIRMA E. HOPMANS, Wieringerwerf (NL)

(72) Inventor: Rudolf Johannes Hopmans, Wieringerwerf (NL)

(73) Assignee: FIRMA E. HOPMANS V.O.F., Wieringerwerf (NL)

( * ) Notice: Subject to any disclaimer, the term of this patent is extended or adjusted under 35 U.S.C. 154(b) by 0 days.

(21) Appl. No.: 18/199,081

(22) Filed: May 18, 2023

(65) Prior Publication Data

US 2023/0380313 P1 Nov. 23, 2023

Related U.S. Application Data

(60) Provisional application No. 63/344,425, filed on May 20, 2022.

(51) Int. Cl.
*A01H 5/02* (2018.01)
*A01H 6/68* (2018.01)

(52) U.S. Cl.
USPC ..... Plt./251
CPC ..... *A01H 6/68* (2018.05); *A01H 5/02* (2013.01)

(58) Field of Classification Search
USPC ..... Plt./251
See application file for complete search history.

(56) References Cited

PUBLICATIONS https://www.tuincentrumbull.nl/product/330062/hebe-donna-elsa-addenda-pot-23-cm (retrieved from the internet on Dec. 20, 2023).*
https://pluto.upov.int/result; citation for 'HOP107'; (retrieved from the internet on Dec. 20, 2023).*
https://online.plantvarieties.eu/publicConsultationDetails?registerId=20211074&denomination=HOP107&speciesIds=HEB01 (Retrieved from the internet on Dec. 20, 2023).*

* cited by examiner

*Primary Examiner* — Shubo (Joe) Zhou
*Assistant Examiner* — Zachariah Allan Kay
(74) *Attorney, Agent, or Firm* — C. Anne Whealy

(57) ABSTRACT

A new and distinct cultivar of *Hebe* plant named 'HOP107', characterized by its compact and upright to outwardly spreading and uniformly mounding plant habit; freely branching habit; dark green-colored leaves; freely flowering habit with numerous purplish pink-colored flowers; and long flowering period.

1 Drawing Sheet

Botanical designation: *Hebe speciosa Hebe* Comm. ex. Juss.

Cultivar denomination: 'HOP107'.

CROSS-REFERENCED TO CLOSELY-RELATED APPLICATIONS

A European Community Plant Breeder's Rights application for the instant plant was filed by the Applicant/Assignee, Firma E. Hopmans of Wieringerwerf, The Netherlands on Apr. 20, 2021, application number 2021/1074. Foreign priority is not claimed to this application.

BACKGROUND OF THE INVENTION

The present invention relates to a new and distinct cultivar of *Hebe* plant, botanically known as *Hebe speciosa Hebe* Comm. ex. Juss., typically grown as a potted plant and hereinafter referred to by the name 'HOP107'.

The new *Hebe* plant is a product of a planned breeding program conducted by the Inventor in Wieringerwerf, The Netherlands. The objective of the breeding program is to develop new compact *Hebe* plants with attractive flowers.

The new *Hebe* plant is a naturally-occurring branch mutation of *Hebe* Comm. ex. Juss. 'Zebora', not patented. The new *Hebe* plant was discovered and selected by the Inventor on a single flowering plant from within a population of plants of 'Zebora' grown in a controlled greenhouse environment in Wieringerwerf, The Netherlands in October, 2018.

Asexual reproduction of the new *Hebe* plant by terminal stem cuttings in a controlled environment in Wieringerwerf, The Netherlands since February, 2019 has shown that the unique features of this new *Hebe* plant are stable and reproduced true to type in successive generations.

SUMMARY OF THE INVENTION

Plants of the new *Hebe* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HOP107'. These characteristics in combination distinguish 'HOP107' as a new and distinct *Hebe* plant:

1. Compact and upright to outwardly spreading and uniformly mounding plant habit.
2. Freely branching habit.
3 Dark green-colored leaves.

4. Freely flowering habit with numerous purplish pink-colored flowers.
5. Long flowering period.

Plants of the new *Hebe* differ primarily from plants of the mutation parent, 'Zebora', in flower color as plants of the new *Hebe* have purplish pink-colored flowers whereas plants of 'Zebora' have bluish purple-colored flowers.

Plants of the new *Hebe* can be compared to plants of *Hebe* Comm. ex. Juss. 'Zita', not patented. In side-by-side comparisons, plants of the new *Hebe* differ primarily from plants of 'Zita' in plant habit as plants of the new *Hebe* are more compact than and not as upright as plants of 'Zita'. In addition, plants of the new *Hebe* have smaller leaves than plants of 'Zita'.

Plants of the new *Hebe* can also be compared to plants of *Hebe* Comm. ex. Juss. 'HOP102', disclosed in U.S. Plant Pat. No. 34,444. In side-by-side comparisons, plants of the new *Hebe* differ primarily from plants of 'HOP102' in flower color as plants of the new *Hebe* have purplish pink-colored flowers whereas plants of 'HOP102' have purplish red-colored flowers.

BRIEF DESCRIPTION OF THE PHOTOGRAPH

The accompanying colored photograph illustrates the overall appearance of the *Hebe* plant showing the colors as true as it is reasonably possible to obtain in colored reproductions of this type. Colors in the photograph may differ slightly from the color values cited in the detailed botanical description which accurately describe the actual colors of the new *Hebe* plant.

The photograph is a side perspective view of a typical flowering plant of 'HOP107' grown in a container.

DETAILED BOTANICAL DESCRIPTION

Plants used for the aforementioned photograph and following description were grown in 13-cm containers during the summer and early autumn in a glass-covered greenhouse in Wieringerwerf, The Netherlands and under cultural practices typical of commercial *Hebe* production. During the production of the plants, day temperatures ranged from 16 C. to 20 C. and night temperatures ranged from 12 C. to 16 C. Plants were pinched one time about one month after planting and were five months old when the photograph and the description were taken. In the following description, color references are made to The Royal Horticultural Society Colour Chart, 2015 Edition, except where general terms of ordinary dictionary significance are used.

Botanical classification: *Hebe* Comm. ex. Juss. 'HOP107'.

Parentage: Naturally-occurring branch mutation of *Hebe* Comm. ex. Juss. 'Zebora', not patented.

Propagation:

*Type cutting.*—Terminal stem cuttings.

*Time to initiate roots, summer.*—About ten days at temperatures about 18 C.

*Time to initiate roots, winter.*—About 14 days at temperatures about 20 C.

*Time to produce a rooted young plant, summer.*—About 40 days at temperatures about 18 C.

*Time to produce a rooted young plant, winter.*—About 50 days at temperatures about 20 C.

*Root description.*—Medium in thickness, fleshy; typically white to brown in color, actual color of the roots is dependent on substrate composition, water quality, fertilizer type and formulation, substrate temperature and physiological age of roots.

*Rooting habit.*—Moderately freely branching; medium density.

Plant description:

*Plant type.*—Evergreen perennial shrub.

*Plant and growth habit.*—Compact and upright to outwardly spreading and uniformly mounding plant habit; vigorous growth habit and moderate to rapid growth rate.

*Plant height, soil level to top of foliar plane.*—About 20.6 cm.

*Plant height, soil level to top of floral plane.*—About 21.1 cm.

*Plant width.*—About 37.7 cm.

*Lateral branch description.*—Branching habit: Freely branching habit with about six primary branches, each with about eleven secondary branches; pinching enhances lateral branching potential. Length (excluding inflorescence): About 8.8 cm. Diameter: About 3.5 mm. Internode length: About 1.7 cm. Strength: Strong. Aspect: Erect to about 55 degrees from vertical. Texture and luster: Densely pubescent; slightly glossy. Color, developing: Close to 144B. Color, developed: Close to a blend of 177A and 178A; towards the base, close to 200B; at the internodes, close to 183C.

Leaf description:

*Arrangement.*—Opposite, simple.

*Length.*—About 4.8 cm.

*Width.*—About 2.2 cm.

*Shape.*—Elliptic to close to oblong.

*Apex.*—Bluntly acute.

*Base.*—Cuneate.

*Margin.*—Entire; slightly revolute and slightly and coarsely undulate; not lobed.

*Texture and luster, upper surface.*—Smooth, glabrous; not rugose; moderately glossy.

*Texture and luster, lower surface.*—Smooth, glabrous; not rugose; slightly glossy.

*Venation pattern.*—Pinnate.

*Color.*—Developing leaves, upper surface: Close to between 144A and 146A; towards the margins and midvein, close to 176A and 176B. Developing leaves, lower surface: Close to 148B slightly tinged with close to 176B; towards the margins, close to 178A; midvein, close to 183A. Fully expanded leaves, upper surface: Close to NN137B; towards the base, close to 145A; narrow margins, close to 177A; venation, close to N200B. Fully expanded leaves, lower surface: Close 146B; narrow margins, close to 177A; venation, close to 183B.

*Petioles.*—Length: About 2 mm. Diameter: About 2 mm by 4.5 mm. Strength: Strong. Texture and luster, upper and lower surfaces: Smooth, glabrous; slightly glossy. Color, upper surface: Close to 145A tinged with close to 177D. Color, lower surface: Close to 146B to 146C tinged with close to 183A.

Flower description:

*Flower arrangement and shape.*—Single campanulate flowers arranged on dense axillary racemes; flowers face mostly outwardly.

*Flowering habit.*—Freely flowering habit with about 100 flowers developing per inflorescence and about 7,200 flowers developing per plant during the flowering season.

*Fragrance.*—None detected.

*Natural flowering season.*—Plants begin flowering about 140 days after planting; plants flower continuously from the summer into the autumn in The Netherlands.

*Flower longevity.*—Flowers last about one week on the plant; flowers not persistent.

*Flower buds.*—Length: About 5 mm. Diameter: About 2 mm. Shape: Oblong. Texture and luster: Moderately to densely pubescence; matte. Color: Developing sepals, close to 147B tinged with close to 183B; developing petals, close to 63B.

*Inflorescence height* (*length*).—About 6.4 cm.

*Inflorescence diameter.*—About 2.6 cm.

*Flower diameter.*—About 6 mm by 6.5 mm.

*Flower height.*—About 1 cm.

*Throat diameter.*—About 2 mm.

*Tube length.*—About 1.5 mm.

*Tube diameter.*—About 2 mm.

*Petals.*—Quantity and arrangement: Four arranged in a single whorl; petals fused about 30% of the petal length from the base. Length, all petals: About 6.5 mm. Width, upper petal: About 3.5 mm. Width, lateral petals: About 3 mm. Width, lower petal: About 2 mm. Shape, upper and lateral petals: Obovate; slightly concave. Shape, lower petal: Narrowly obovate; slightly concave. Apex, upper petal: Obtuse. Apex, lateral and lower petals: Bluntly acute. Margin: Entire; slightly involute; not undulate. Texture and luster, upper surface: Smooth, glabrous; matte. Texture and luster, lower surface: Smooth, glabrous; slightly glossy. Texture and luster, throat and tube: Smooth, glabrous; slightly glossy. Color: When opening, upper surface: Close to N66C. When opening, lower surface: Close to N66D. Fully opened, upper surface: Close to 68B; venation, close to 68B; color becoming closer to 73D with subsequent development. Fully opened, lower surface: Close to 68B to 68C; venation, close to 68B to 68C; color becoming closer to 73D with subsequent development. Throat: Close to 77B; venation, close to 77B. Tube: Close to a 77B and N78C; venation, close 77B and N78C; color becoming closer to 77C with subsequent development.

*Sepals.*—Quantity and arrangement: Four arranged in a single whorl and fused at the base. Length: About 3 mm. Width: About 1.25 mm. Shape: Narrowly ovate to close to oblong. Apex: Acute. Base: Cuneate, fused. Margin: Entire. Texture and luster, upper surface: Smooth, glabrous; matte. Texture and luster, lower surface: Moderately to densely pubescent; matte. Color: When opening and fully opened, upper surface: Close to 146B. When opening and fully opened, lower surface: Close to 147B slightly tinged with close to 183B.

*Peduncles.*—Length: About 8.3 cm. Diameter: About 2 mm. Aspect: About 55 degrees from stem axis. Strength: Strong. Texture and luster: Densely pubescent; slightly glossy. Color: Close to 146B; proximally, close to 183A.

*Pedicels.*—Length: About 3 mm. Diameter: About 0.5 mm. Aspect: About 70 degrees from peduncle axis. Strength: Moderately strong. Texture and luster: Densely pubescent; matte. Color: Close to 146B.

*Flower bracts.*—Quantity and arrangement: One at the base of each flower. Length: About 3 mm. Width: About 1 mm. Shape: Narrowly ovate. Apex: Acute. Base: Cuneate. Margin: Entire. Texture, upper and lower surfaces: Smooth, glabrous. Color, upper and lower surfaces: Close to 146B.

*Reproductive organs.*—Stamens: Quantity per flower: Two. Filament length: About 8 mm. Filament color: Close to 64C. Anther size: About 0.75 mm by 2 mm. Anther shape: Oblong. Anther color: Close to N77B. Pollen amount: None detected. Pistils: Quantity per flower: One. Pistil length: About 8 mm. Stigma diameter: About 5 mm. Stigma shape: Club-shaped. Stigma color: Greyish white. Style length: About 7.95 mm. Style color: Close to 72A. Ovary color: Close to 143C.

*Seeds and fruits.*—To date, seed and fruit development has not been observed on plants of the new *Hebe*.

Pathogen & pest resistance: To date, plants of the new *Hebe* have not been noted to be resistant to pathogens and pests common to *Hebe* plants.

Garden performance: Plants of the new *Hebe* have exhibited good garden performance and to be tolerant to rain, wind, temperatures ranging from about −7 C to about 40 C and to be suitable for USDA Hardiness Zones 8 to 11.

It is claimed:

1. A new and distinct *Hebe* plant named 'HOP107' as illustrated and described.

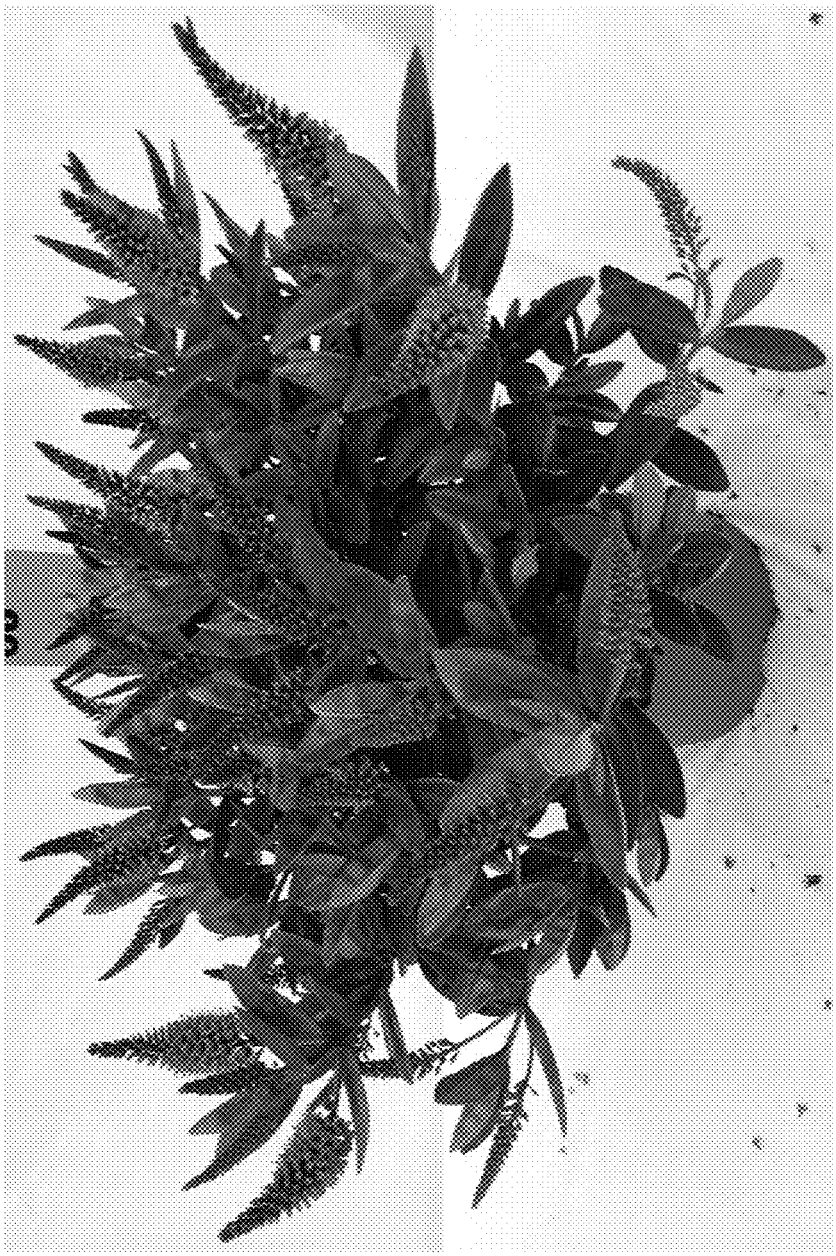

* * * * *